US007271781B2

(12) United States Patent
Fischer et al.

(10) Patent No.: US 7,271,781 B2
(45) Date of Patent: Sep. 18, 2007

(54) **MULTIPLEX HYBRIDIZATION SYSTEM FOR IDENTIFICATION OF PATHOGENIC *MYCOBACTERIUM* AND METHOD OF USE**

(75) Inventors: Steven H. Fischer, Rockville, MD (US); Jang B. Rampal, Yorba Linda, CA (US); Gary A. Fahle, Silver Spring, MD (US); Patricia S. Conville, Rockville, MD (US)

(73) Assignees: The United States of America as Represented by the Secretary of the Department of Health and Human Services, Washington, DC (US); Beckman Coulter, Inc., Fullerton, CA (US)

( * ) Notice: Subject to any disclaimer, the term of this patent is extended or adjusted under 35 U.S.C. 154(b) by 465 days.

(21) Appl. No.: 10/220,212

(22) PCT Filed: Mar. 1, 2001

(86) PCT No.: PCT/US01/06731

§ 371 (c)(1),
(2), (4) Date: Aug. 27, 2002

(87) PCT Pub. No.: WO01/66797

PCT Pub. Date: Sep. 13, 2001

(65) Prior Publication Data

US 2004/0110129 A1 Jun. 10, 2004

Related U.S. Application Data

(60) Provisional application No. 60/186,840, filed on Mar. 3, 2000.

(51) Int. Cl.
*C12Q 1/68* (2006.01)
(52) U.S. Cl. .................................. 345/6; 435/91.2
(58) Field of Classification Search ............... 435/6, 435/91.1, 91.2; 536/24.32
See application file for complete search history.

(56) References Cited

U.S. PATENT DOCUMENTS

| 5,422,252 A | 6/1995 | Walker et al. |
| 5,457,027 A | 10/1995 | Nadeau et al. |
| 5,470,723 A | 11/1995 | Walker et al. |
| 5,521,300 A * | 5/1996 | Shah et al. ............... 536/24.32 |
| 5,554,501 A | 9/1996 | Coassin et al. |
| 5,561,044 A | 10/1996 | Walker et al. |
| 5,583,211 A | 12/1996 | Coassin et al. |
| 5,612,473 A | 3/1997 | Wu et al. |
| 5,624,825 A | 4/1997 | Walker et al. |
| 5,654,143 A * | 8/1997 | Mallet et al. ............... 435/6 |
| 5,667,994 A | 9/1997 | Dilly et al. |
| 5,736,365 A | 4/1998 | Walker et al. |
| 5,811,269 A | 9/1998 | Nadeau et al. |
| 5,849,901 A | 12/1998 | Mabilat et al. |
| 5,861,256 A | 1/1999 | Glass et al. |
| 5,908,744 A | 6/1999 | McAllister et al. |
| 5,981,185 A | 11/1999 | Matson et al. |
| 5,985,567 A | 11/1999 | Rampal |
| 5,985,569 A | 11/1999 | Foxall et al. |
| 6,013,789 A | 1/2000 | Rampal |

FOREIGN PATENT DOCUMENTS

| EP | 0669402 A2 | 2/1995 |
| EP | 0640691 | 3/1995 |
| EP | 0669402 | 8/1995 |
| EP | 0 851 033 | 7/1998 |
| EP | 1 227 152 A1 | 7/2002 |
| WO | WO95/33851 | 12/1995 |
| WO | WO96/26276 A1 | 8/1996 |
| WO | WO97/08340 | 3/1997 |
| WO | WO99/2023 | 5/1999 |
| WO | WO99/22023 | 5/1999 |
| WO | WO01/92573 A1 | 12/2001 |
| WO | WO02/077183 A2 | 10/2002 |

OTHER PUBLICATIONS

DeBeenhouwer et al. Journical of Clinical Microbiology. vol. 33:2994-2998. Nov. 1995.*
Buck et al. Biotechniques. vol. 27:529-536. 1999.*
Fiss et al. Journal of Clinical Microbiology vol. 30:1220-1224. 1992.*
Kox et al. Journal of Clinical Microbiology vol. 35:1492-1498. 1997.*
Aoki et al., "Efficacy of PCR-Microwell Plate Hybridization Method (Amplicor Mycobacterium) for Detection of M. tuberculosis, M. avium, and/or M. intracellulare in Clinical Specimens," *Kekkaku* 69(10):593-605, Oct. 1994. (abstract only).
Coutlée et al., "Nonisotopic Detection and Typing of Human Papillomavirus DNA in Genital Samples by the Line Blot Assay," *Journal of Clinical Microbiology* 37(6):1852-1857, Jun. 1999.
De Beenhouwer et al., "Detection and Identification of Mycobacteria by DNA Amplification and Oligonucleotide-Specific Capture Plate Hybridization," *Journal of Clinical Microbiology* 33(11):2994-2998, Nov. 1995.
Ishiko, "Rapid Identification of Bacteria by PCR and Hybridization," *Nippon Rinsho* 52(2):344-349, Feb. 1994. (abstract only).
Stuyver et al., "Second-Generation Line Probe Assay for Hepatitis C Virus Genotyping," *Journal of Clinical Microbiology* 34(9):2259-2266, Sep. 1996.

(Continued)

Primary Examiner—Gary Benzion
Assistant Examiner—Heather Calamita
(74) Attorney, Agent, or Firm—Klarquist Sparkman, LLP

(57) ABSTRACT

A method for species-specific identification of a *Mycobacterium* species is provided. Also disclosed is a method for identifying the species of *Mycobacterium* present in a sample. A device is disclosed for the detection of *Mycobacterium*. *Mycobacterium*-specific oligonucleotides are also disclosed, as are kits.

14 Claims, 3 Drawing Sheets

OTHER PUBLICATIONS

Tevere et al., "Detection of *Mycobacterium tuberculosis* by PCR Amplification with Pan-*Mycobacterium* Primers and Hybridization to an *M. tuberculosis* -Specific Probe," *Journal of Clinical Microbiology* 34(4):918-923, Apr. 1996.

van der Vliet et al., "Nucleic Acid Sequence-Based Amplification (NASBA) for the Identification of Mycobacteria," *J. Gen. Microbiol.* 139(10):2423-2429, Oct. 1993. (abstract only).

Wilton et al., "Detection and Identification of Multiple Mycobacterial Pathogens by DNA Amplification in a Single Tube," *PCR Methods Appl.* 1(4):269-273, May 1992. (abstract only).

Yamamoto et al., "Polymerase Chain Reaction for the Differentiation of *Mycobacterium Intracellular* and *Mycobacterium Avium* ," *Tuber Lung Dis.* 74(5):342-345, Oct. 1993. (abstract only).

Braunstein et al., "Two Nonredundant SecA Homologues Function in Mycobacteria," *Journal of Bacteriology*, 183(24):6979-6990, 2001.

Zelazny et al., "Identification of *Mycobacterium* Species by secA1 Sequences," *Journal of Clinical Microbiology*, 43(3):1051-1058, 2005.

\* cited by examiner

MULTIPLEX HYBRIDIZATION SYSTEM FOR IDENTIFICATION OF PATHOGENIC *MYCOBACTERIUM* AND METHOD OF USE

PRIORITY CLAIM

This is a §371 U.S. national stage of PCT/US01/06731, filed Mar. 1, 2001, which was published in English under PCT Article 21(2), and claims the benefit of U.S. Application No. 60/186,840, filed Mar. 3, 2000.

FIELD

This disclosure relates to a method of detecting mycobacterial infection in a subject. In one embodiment, the method allows the identification of the *Mycobacterium* species involved in the infection.

BACKGROUND

The genus *Mycobacterium* is responsible for more disease world-wide than all other bacterial genera combined. Mycobacteria are small, 0.5×1 μm, weakly gram-positive bacilli that have two characteristic bacteriologic features. First, the cell walls of these organisms contain very long chain fatty acid esters known as mycolic acids (lipids typically having chain lengths of 70 to 90 carbons). This unusual cell envelope allows the mycobacteria to be impervious to many antiseptic solutions and antibiotics. Secondly, the pathogenic mycobacteria have an unusually slow growth rate. Unlike typical bacterial pathogens such as *E. coli* or *Staphylococcus aureus*, which double in 20-30 minutes and grow to high densities overnight in culture media, *M. avium* and *M. tuberculosis* double approximately every 24 hours. Thus it can take three to four weeks to obtain a dense liquid culture or a visible colony of mycobacteria on a plate. The best known property of the genus is the ability of the bacteria to resist decolorization by weak acids after staining, hence the term "acid-fast bacilli" (Wayne "Cultivation of *Mycobacterium tuberculosis* for research purposes", in *Tuberculosis: Pathogenesis, Protection, and Control*, ASM Press, Bloom BR (ed), Washington, D.C., 1994, pp. 73-84).

Within the genus *Mycobacteria*, there are a number of closely related species that have been grouped into complexes. Currently, over 60 species of mycobacteria have been well defined. Species other than *M. tuberculosis* and *M. leprae* have been termed the "environmental mycobacteria," many of which are known pathogens. For example, *M. kansasii* is an important pulmonary pathogen, along with the *M. avium* complex.

The *Mycobacterium avium* complex (MAC) includes two species, *M. avium* and *M. intracellulare*. Though *M. avium* was originally identified as a pathogen of birds, it is now known that both *M. avium* and *M. intracellulare* are environmental saprophytes that survive well in soil, water, and food, and can be carried by animals (Inderlied et al., *Clin Microbiol Rev* 6:266-310, 1993; Shinnick and Good, *Eur. J. Clin. Microbiol. Infect. Dis.* 13:884-901, 1994).

MAC is an opportunistic, rather than innate, pathogen in humans; it causes disease primarily in immuno-compromised patients. MAC causes three classical disease syndromes: disseminated MAC, pulmonary MAC, and MAC cervical lymphadenitis, the most common of which is disseminated MAC (Horsburgh, "Epidemiology of *Mycobacterium avium* complex," in *Mycobacterium avium Complex Infection: Progress in Research and Treatment*, Marcel Dekker, Inc., Korvick and Benson (eds), New York, 1996, pp. 1-22.

The *Mycobacterium tuberculosis* complex includes *M. tuberculosis*, *M. bovis*, *M. africanum*, and *M. microti*. Each of these species, except *M. microti* (a cause of rodent tuberculosis), causes tuberculosis in humans. Significantly, there are no environmental reservoirs of *M. tuberculosis* complex organisms, and only a few animals (cattle and occasionally deer) transmit tuberculosis to humans. Of all the culturable mycobacteria, only *M. tuberculosis* is an obligate pathogen.

*M. tuberculosis* causes a variety of disease syndromes depending upon the site of infection. The lung is the site of initial tuberculous infection and pulmonary tuberculosis remains the most common presentation, accounting for 85% of all tuberculosis in non-HIV infected patients. Pulmonary tuberculosis (TB) is the leading cause of death due to a single infectious organism in the world. There are 8 to 10 million new active cases of TB each year and approximately two million deaths. It is believed that one-third of the world's population, or 1.7 billion individuals, harbor latent tuberculosis (Centers for Disease Control and Prevention: Tuberculosis morbidity—United States, 1997. MMWR 47(13):253-7, 1998; Small et al., *N. Engl. J. Med.* 324:289-94, 1991).

Leprosy is caused by *M. leprae*, a slow growing obligate intracellular parasite. The disease is believed to occur as a result of a relatively specific defect in a patient's cell-mediated immune response to *M. leprae*. There are 11 to 12 million cases of leprosy worldwide; the United States has more than 5,500. Diagnosis of leprosy is based on physical findings plus skin scrapings and biopsy. Skin scrapings are evaluated by smearing the material onto a microscopic slide and histological staining (see below). Once diagnosed, leprosy can be treated using a combination anti-leprosy drug therapy (Jacobson, "Leprosy," In: *Textbook of Internal Medicine*, Kelley et al. (eds.), J.B. Lippincott Co., 1989, pp. 1582-4).

In general, a combination therapy is essential for the effective treatment of TB or MAC disease, although different agents are used to treat the different infections. The identification of the species of mycobacteria involved in an infection is essential to determining the treatment protocol. For example, MAC organisms are resistant to many of the standard anti-mycobacterial drugs used for tuberculosis, including isoniazid, pyrazinamide, and often streptomycin.

The two laboratory techniques that have classically been used to detect a mycobacterial infection are the acid fast smear and cultivation of the organism. In addition, techniques have been developed to determine the species of the organism (e.g. DNA blotting techniques). Generally, these techniques are performed on a body fluid, such as sputum and blood (Heifets and Good, "Current laboratory methods for the diagnosis of tuberculosis," in: *Tuberculosis: Pathogenesis, Protection and Control*. ASM Press, Bloom BR (ed), Washington, D.C., 1994, pp. 85-110).

Smear examinations (such as sputum smears) are usually performed within 24 hours after the specimen is submitted. Smear exams are more rapid but less sensitive than culture. Smears detect 10,000-100,000 organisms per ml of fluid or tissue. Although a negative smear does not rule out disease, it does suggest that the infection is light if it is present at all. Positive smears cannot differentiate between MAC, *M. tuberculosis*, or a host of other environmental acid-fast bacilli, and thus, they must be evaluated on the basis of the case history, as well as physical and laboratory findings.

The cultivation of mycobacteria is time-consuming. It usually takes three to four weeks to obtain colonies on standard semi-solid medium. Most laboratories in the U.S.

use the BACTEC™ radiometric mycobacterial growth system, which detects the growth of mycobacteria by their metabolic conversion of radioactive palmitic acid in the liquid growth medium into radioactive gaseous $CO_2$. The BACTEC™ system frequently yields positive cultures with 8-15 days. However, the BACTEC™ system does not differentiate between *M. tuberculosis* infection, MAC, and other slow-growing mycobacterial infections (Kent and Kubica, *Public Health Mycobacteriology: a Guide for the Level III Laboratory*, US Dept. of Health and Human Services, Atlanta, Ga., 1985; Siddiqi, Radiometric (BACTEC) tests for slowly growing mycobacteria, in: Clinical Microbiology Procedures Handbook, Vol. 1, Isenberg HD (ed), American Society for Microbiology, Washington, D.C., 1992). This is a serious clinical problem because appropriate therapy (and the need for precautionary respiratory isolation) often depends on the species of *Mycobacterium* that is present.

Determining the *Mycobacterium* species present in a sample has been accomplished in the past by removing a small portion of the organism that has grown in the BACTEC™ bottle, and performing a series of DNA hybridization tests with species-specific probes. The DNA probe test (e.g. AccuProbe Kit) takes approximately four hours and can usually be performed a few days after detection of the organism in the BACTEC™ system (Centers for Disease Control and Prevention: Nucleic Acid Amplification Tests for Tuberculosis. MMWR 45:950-952, 1996). Alternatively, a battery of time consuming biochemical and selective medium growth tests can be performed in order to speciate acid fast isolates. However, these procedures often require growth of the bacteria, a process which is time consuming because of the slow growth of mycobacterial organisms.

Nucleic acid amplification methods have been used to identify *M. tuberculosis* in a sample (e.g. U.S. Pat. No. 5,811,269; U.S. Pat. No. 5,736,365). However, there remains a need in the art for a rapid method for detecting the other species of *Mycobacterium* in samples, so that appropriate therapy and any necessary precautions can be initiated and/or terminated as soon as possible. In addition, a need exists for a method to provide rapid identification of not just one species, but multiple species of *Mycobacterium*, particularly those species that are pathogenic, such as known human pathogens.

SUMMARY

A novel method of detecting and diagnosing mycobacterial infection has been developed. This method allows the identification of the species of *Mycobacterium* involved in an infection by detecting the presence of *Mycobacterium* nucleic acids in a sample with a unique solid phase nucleic acid array of *Mycobacterium* specific probes. Both the oligonucleotides used with the method and the solid phase nucleic acid array of *Mycobacterium* specific probes are also disclosed.

A method for species-specific identification of a *Mycobacterium* species, is provided. The method includes: hybridizing a primer which is a *Mycobacterium*-genus selective primer or a *Mycobacterium* specific primer to a sample, amplifying *Mycobacterium*-specific nucleic acids from the sample utilizing the *Mycobacterium*-genus selective primer or the *Mycobacterium* specific primer to produce amplified *Mycobacterium*-specific nucleic acids, hybridizing the amplified *Mycobacterium* specific nucleic acids to a solid phase nucleic acid array comprising a plurality of *Mycobacterium* species specific probe oligonucleotides chemically linked to a polymeric solid support surface in a predetermined pattern, detecting a hybridization pattern of the *Mycobacterium*-specific nucleic acid to the *Mycobacterium* species specific probe oligonucleotides chemically linked to a solid support surface in a predetermined pattern, and identifying the species of *Mycobacterium* in the sample based on the hybridization pattern.

Also disclosed is a method for identifying a species of *Mycobacterium* present in a sample. The method includes providing a plurality of single stranded *Mycobacterium* species-specific oligonucleotides probes chemically linked to a solid support surface in an array. A *Mycobacterium* nucleic acid from the sample is hybridized with the array, wherein the *Mycobacterium* nucleic acid is in solution, and forms a hybridization complex with a species-specific probe in the array. The presence of the hybridization complex is detected, wherein the presence of the hybridization complex in the array indicates the species of *Mycobacterium* present in the sample. In some embodiments, the *Mycobacterium*-specific nucleic acid in the sample can be amplified prior to the hybridization step.

A device is also disclosed for the detection of *Mycobacterium*. The device includes a solid phase nucleic acid array comprising a plurality of *Mycobacterium* species specific oligonucleotides chemically linked to a solid polymeric support surface in a predetermined pattern.

*Mycobacterium*-specific oligonucleotides are disclosed, which can be used as probes in the array. These oligonucleotides include those that have a sequence comprising at least 15 consecutive base pairs of any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10. SEQ ID NO: 11, SEQ ID NO: 12, SEQ ID NO: 13, SEQ ID NO: 14, SEQ ID NO: 15, SEQ ID NO: 16 SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, or SEQ ID NO: 33.

The foregoing and other objects, features and advantages of the disclosure will become more apparent from the following detailed description, which proceeds with reference to the following detailed description of several particular embodiments, as illustrated in the accompanying drawings.

BRIEF DESCRIPTION OF THE DRAWINGS

FIG. 2A is a linear pattern of probe oligonucleotides. FIG. 2B is a slot (rectangular) pattern of probe oligonucleotides. FIG. 2C is a circular (dot) pattern of probe oligonucleotides.

FIG. 3A *M. gordonae* (12); FIG. 3B

*M. intracellulare* (14); FIG. 3C *M. avium* (16) FIG. 3D *M. tuberculosis* (18); FIG. 3E *M. ulceran* (20); FIG. 3F *M. marinum* (22); FIG. 3G *M. kansasii* (24); and FIG. 3H *M gastri* (26).

FIGS. 4A-4D show the standard reaction with non-biotin dCTP and FIGS. 4E-4H show the reaction using biotin labeled dCTP. FIGS. 4A and 4E, undiluted; FIGS. 4B and 4F 1:10 dilution; FIGS. 4C and 4G, 1:100 dilution; and FIGS. 4D and 4H, 1:1000 dilution.

SEQUENCE LISTING

Figure 1:
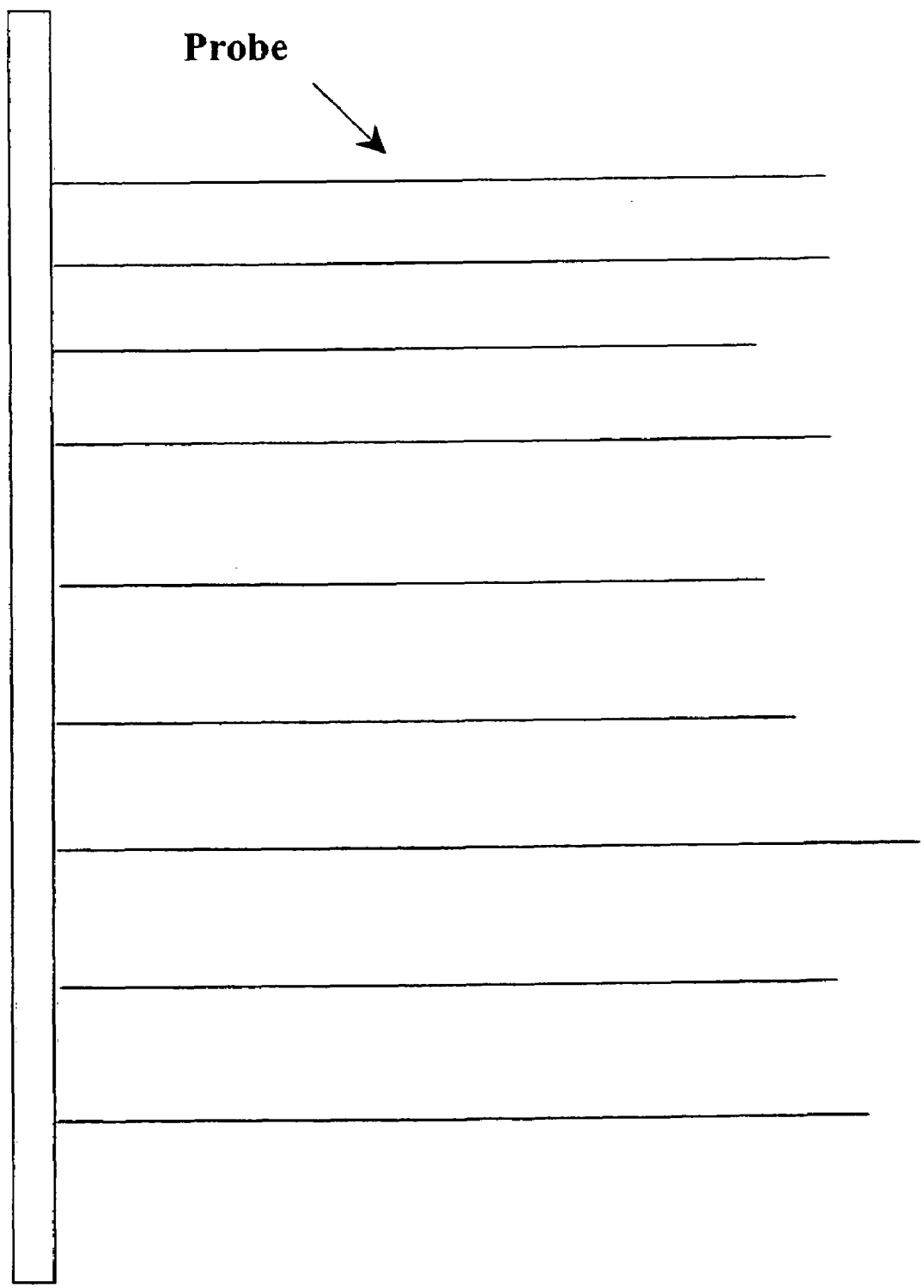
FIG. 1 is a schematic drawing showing a side view of a solid phase array, illustrating *Mycobacterium* oligonucleotide probes attached to a solid support.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1 is an example of a *Mycobacterium* genus selective primer, such as a *Mycobacterium*-specific upstream primer.

SEQ ID NO: 2 is a *Mycobacterium* genus selective primer.

SEQ ID NOS: 3-9 are examples of *Mycobacterium* specific primers, such as downstream primers.

SEQ ID NOS: 10-20 are *Mycobacterium* species-specific probes that can be used to detect *M. gordonae; M. intracellulare*-1*; M. intracellulare*-2*; M. avium/M. paratuberculosis; M. tuberculosis; M. ulcerans/M. marinum; M. kansasii/M. gastri/M. scrofulaceum; M. haemophilum; M. leprae; M. genavense* and *M. xenopi*, respectively.

SEQ ID NOS: 21-33 are other *Mycobacterium* species specific probes which can be used to detect *M. fortuitum*-1; *M. fortuitum*-1RC; *M. fortuitum*-2; *M. fortuitum*-2RC; *M. fortuitum*-3; *M. fortuitum*-3RC; *M. fortuitum*-4; *M. fortuitum*-4RC; *M. fortuitum*-5; *M. fortuitum*-5RC; *M. chelonae*-1; *M. chelonae*-2 and *M. chelonae*-3, respectively.

SEQ ID NO: 34 is the nucleic acid sequence of a *Mycobacterium tuberculosis* 16S rRNA gene, subspecies caprae, Genbank Accession No. AJ131120.

SEQ ID NO: 35 is the nucleic acid sequence of a *Mycobacterium gordonae* 16S ribosomal RNA gene, Genbank Accession No. AF115387.

DETAILED DESCRIPTION OF THE SPECIFIC EMBODIMENTS

I. Terms

Unless otherwise noted, technical terms are used according to conventional usage. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The following terms and methods are provided to better define the present disclosure, and to guide those of ordinary skill in the art in the practice of the present disclosure. As used in this specification and in the appended claims, the singular forms "a", "an", and "the" include plural referents unless the context clearly dictates otherwise. Thus, for example, reference to "a cell" includes a plurality of such cells and reference to "the primer" includes reference to one or more primers and equivalents thereof known to those skilled in the art, and so forth.

Animal: Living multicellular vertebrate organisms, a category that includes, for example, mammals and birds.

Antisense and Sense: Double-stranded DNA (dsDNA) has two strands, a 5'->3' strand, referred to as the plus strand, and a 3'->5' strand, referred to as the minus strand. Because RNA polymerase adds nucleic acids in a 5'->3' direction, the minus strand of the DNA serves as the template for the RNA during transcription. Thus, the RNA formed will have a sequence complementary to the minus strand, and identical to the plus strand (except that the base uracil is substituted for thymine).

Antisense molecules are molecules that are specifically hybridizable or specifically complementary to either RNA or the plus strand of DNA. Sense molecules are molecules that are specifically hybridizable or specifically complementary to the minus strand of DNA.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including functional or physical binding assays. Binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, a method which is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target dissociate or melt.

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

Biological Specimen: A biological specimen is a sample of bodily fluid or tissue used for laboratory testing or examination. As used herein, biological specimens include all clinical samples useful for detection of microbial infection in subjects. A biological specimen can be a biological fluid. Biological fluids include blood, derivatives and fractions of blood such as serum, and fluids of the respiratory tract, including the oropharyngeal tract, such as sputum that has been expectorated or collected during bronchoscopy.

Examples of appropriate specimens for use with the current disclosure for the detection of *Mycobacterium* include conventional clinical samples, for instance blood or blood-fractions (e.g., serum), and bronchoalveolar lavage (BAL), sputum, and induced sputum samples. Techniques for acquisition of such samples are well known in the art. Blood and blood fractions (e.g., serum) can be prepared in traditional ways. Oropharyngeal tract fluids can be acquired through conventional techniques, including sputum induction, bronchoalveolar lavage (BAL), and oral washing. Obtaining a sample from oral washing involves having the subject gargle with an amount of normal saline for about 10-30 seconds and then expectorate the wash into a sample cup.

Appropriate tissue samples can be taken, for instance from the skin, lung or bronchial tissue. Samples can be taken by biopsy or during autopsy examination, as appropriate.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

Genetic Target: The terms "gene," "genetic target" and "target nucleic acid" include both DNA and RNA. Generally, a gene is a sequence of DNA or RNA that codes for a protein. A "target" sequence is a sequence to which an antisense or sense oligonucleotide specifically hybridizes.

Hybridization: Oligonucleotides hybridize by hydrogen bonding, which includes Watson-Crick, Hoogsteen or reversed Hoogsteen hydrogen bonding between complementary nucleotide units. For example, adenine and thymine are complementary nucleotides which base pair through formation of hydrogen bonds. "Complementary" refers to sequence complementarity between two nucleotide units. For example, if a nucleotide unit at a certain position of an oligonucleotide is capable of hydrogen bonding with a nucleotide unit at the same position of a DNA or RNA molecule, then the oligonucleotides are complementary to each other at that position. The oligonucleotide and the DNA or RNA are complementary to each other when a sufficient number of corresponding positions in each molecule are occupied by nucleotide units which can hydrogen bond with each other. A "hybridization complex" is formed when complementary nucleotides in a nucleic acid molecule(s) form base pairs.

"Specifically hybridizable" and "complementary" are terms which indicate a sufficient degree of complementarity such that stable and specific binding occurs between the oligonucleotide and the DNA or RNA target. An oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, or under conditions in which an assay is performed.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (1989), chapters 9 and 11, herein incorporated by reference.

For purposes of the present disclosure, "stringent conditions" encompass conditions under which hybridization will only occur if there is less than 25% mismatch between the primer or oligonucleotide probe and the target sequence. "Stringent conditions" can be broken down into particular levels of stringency for more precise definition. Thus, as used herein, "moderate stringency" conditions are those under which molecules with more than 25% sequence variation (also termed "mismatch") will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 5% mismatch will not hybridize.

Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. ((1989) In *Molecular Cloning: A Laboratory Manual*, Cold Spring Harbor, N.Y.) and Tijssen ((1993) *Laboratory Techniques in Biochemistry and Molecular Biology—Hybridization with Nucleic Acid Probes* Part 1, Chapter 2, Elsevier, New York). Nucleic acid molecules that hybridize under stringent conditions to a *Mycobacterium* 16S ribosomal subunit sequence will typically hybridize to a the selected portions of the gene under wash conditions of 2×SSC at 50° C.

Internal Complementarity: The degree of complementarity of an oligonucleotide probe with itself. The internal complementarity of a probe determines the amount of base pairing that will occur within the sequences of the oligonucleotide probe itself, or with an oligonucleotide probe of the identical sequence.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Mammal: This term includes both human and non-human mammals. Similarly, the term "subject" includes both human and veterinary subjects.

Medium: The physical structural shape of a polymer that forms a solid support. Thus, medium can generally include, but are not limited to: polymer films (i.e., polymers having a substantially non-porous surface); polymer filaments (e.g., mesh and fabrics); polymer beads; polymer foams; polymer frits; and polymer threads.

*Mycobacterium* genus-selective primer: A primer that permits amplification of nucleic acid from virtually all members of the *Mycobacterium* genus. In one embodiment, a *Mycobacterium* genus-selective primer includes the nucleic acid sequence shown in SEQ ID NO: 1 and 2.

*Mycobacterium*-specific primer: A primer which permits amplification of nucleic acid from selected clinically relevant mycobacterial pathogens. In one embodiment, these primers amplify sequences for *M. gordonae, M. intracellulare, M. avium, M. tuberculosis, M. marinum*, and *M. kansasii*. In one embodiment, a *Mycobacterium*-specific primer includes the nucleic acid sequence shown in SEQ ID NO: 1 as the upstream primer and SEQ ID NO: 2, 3, 4, 5, 6, 7, 8, or 9 as the downstream primer.

*Mycobacterium* species specific probe or probe oligonucleotide: A probe oligonucleotide that hybridizes to nucleic acid from a specified number of *Mycobacterium* species, but does not bind nucleic acid from all *Mycobacterium* species, under a specified set of hybridization conditions. In one specific, non-limiting example, the probe binds *M. avium/M. paratuberculosis* nucleic acid under a specific set of hybridization conditions, but does not bind nucleic acid from any other *Mycobacterium* under identical hybridization conditions. In one embodiment, the probe oligonucleotide hybridizes with nucleic acid from only one species of *Mycobacterium* (e.g., *M. gordonae*) under a specific set of hybridization conditions, but does not hybridize with nucleic acid from any other species of *Mycobacterium* under identical hybridization conditions.

Nucleic acid sequence (or polynucleotide): A deoxyribonucleotide or ribonucleotide polymer in either single or double stranded form, and unless otherwise limited, encompasses known analogues of natural nucleotides that hybridize to nucleic acids in a manner similar to naturally occurring nucleotides, and includes polynucleotides encoding full length proteins and/or fragments of such full length proteins which can function as a therapeutic agent. A polynucleotide is generally a linear nucleotide sequence, including sequences of greater than 100 nucleotide bases in length. In one embodiment, a nucleic acid is labeled (e.g. biotinylated, fluorescently labeled or radiolabeled nucleotides).

Nucleotide: Nucleotide includes, but is not limited to, a monomer that includes a base linked to a sugar, as in DNA and RNA, or a base linked to an amino acid, as in a peptide nucleic acid (PNA). A nucleotide is one monomer in a polynucleotide. A nucleotide sequence refers to the sequence of bases in a polynucleotide. In one embodiment, nucleotides are labeled (e.g. biotinylated, fluorescently labeled or radiolabeled nucleotides).

Oligonucleotide: A linear polynucleotide sequence of between 10 and 100 nucleotide bases in length. An oligonucleotide can be labeled (e.g using radioactive isotopes, enzyme substrates, co-factors, ligands, chemiluminescent or fluorescent agents, haptens, and enzymes) either at the 3' or the 5' end, or by the incorporation of labeled nucleotides into the oligonucleotide. Examples of oligonucleotides are those which are at least 15, 25, 50, 75 or 90 nucleotide bases in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Organic polymer: A support material which is in one embodiment chemically inert under conditions appropriate for biopolymer synthesis, and which comprises a backbone comprising various elemental substituents including, but not limited to, hydrogen, carbon, oxygen, fluorine, chlorine, bromine, sulfur, and nitrogen. Representative polymers include, but are not limited to: polypropylene, polyethylene, polybutylene, polyisobutylene, polybutadiene, polyisoprene, polyvinylpyrrolidone, polytetrafluoroethylene, polyvinylidene, difluoride, polyfluoroethylene-propylene, poly-ethylene-vinyl alcohol, polymethypentene, polychlorotrifluoroethylene, polysulfones, and blends and copolymers thereof.

ORF (open reading frame): A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. Orthologous sequences are also homologous sequences.

Polypeptide: Any chain of amino acids, regardless of length or post-translational modification (e.g., glycosylation or phosphorylation).

Primers: Nucleic acid primers can be readily prepared based on the nucleic acid molecules provided herein. A primer comprises an isolated nucleic acid. The nucleic acid can be attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, Cold Spring Harbor, N.Y., 1989) and Ausubel et al. (In *Current Protocols in Molecular Biology*, Greene Publ. Assoc. and Wiley-Intersciences, 1992).

Primers are short nucleic acid molecules, such as DNA oligonucleotides 15 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR), or other nucleic-acid amplification methods known in the art.

An "upstream" primer is a primer 5' to a reference point on a nucleic acid sequence. A "downstream" primer is a primer 3' to a reference point on a nucleic acid sequence. In general, at least one upstream and one downstream primer are included in an amplification reaction.

Methods for preparing and using primers are described, for example, in Sambrook et al. (In *Molecular Cloning: A Laboratory Manual*, Cold Spring Harbor, N.Y., 1989), Ausubel et al. (In *Current Protocols in Molecular Biology*, Greene Publ. Assoc. and Wiley-Intersciences, 1992), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, ® 1991, Whitehead Institute for Biomedical Research, Cambridge, Mass.). One of ordinary skill in the art will appreciate that the specificity of a particular primer increases with its length. Thus, for example, a primer comprising 20 consecutive nucleotides of the nucleic acid encoding a *Mycobacterium* 16S ribosomal subunit will anneal to a target sequence, such as a *Mycobacterium* nucleic acid in a sputum sample, with a higher specificity than a corresponding primer of only 15 nucleotides.

The disclosure thus includes isolated nucleic acid molecules that comprise specified lengths of the *Mycobacterium* 16S ribosomal subunit gene sequences. Such molecules can comprise at least 20, 25, 30, 35 or 40 consecutive nucleotides of these sequences, and can be obtained from any region of the disclosed sequences. The *Mycobacterium* 16S ribosomal subunit gene is approximately 1450 nucleotides in length. Nucleic acid molecules can be selected that comprise at least 20, 25, 30, 35 or 40 consecutive nucleotides of any of portions of the *Mycobacterium* 16S ribosomal subunit gene. In one embodiment, nucleic acid primer oligonucleotides are selected from about base pair 100 to about base pair 600 of the *Mycobacterium* 16S ribosomal subunit gene.

Probes: Nucleic acid probes can also be readily prepared based on the nucleic acid molecules provided herein. A probe comprises an isolated nucleic acid. Methods for preparing and using probes are described, for example, in Sambrook et al. (in *Molecular Cloning: A Laboratory Manual*, Cold Spring Harbor, N.Y., 1989), Ausubel et al. (in *Current Protocols in Molecular Biology*, Greene Publ. Assoc. and Wiley-Intersciences, 1992), and Innis et al. (*PCR Protocols, A Guide to Methods and Applications*, Academic Press, Inc., San Diego, Calif., 1990).

One of ordinary skill in the art will appreciate that the specificity of a particular probe also increases with its length. Thus, for example, a probe comprising 20 consecutive nucleotides of the nucleic acid encoding a *Mycobacterium* 16S ribosomal subunit will anneal to a target sequence, such as an amplified *Mycobacterium* nucleic acid, with a higher specificity than a corresponding probe of only 15 nucleotides. Thus, in order to obtain greater specificity, probes and primers can be selected that comprise 20, 25, 30, 35, 40 or more consecutive nucleotides of *Mycobacterium* 16S ribosomal subunit gene sequences.

The disclosure thus includes isolated nucleic acid molecules that comprise specified lengths of the *Mycobacterium* 16S ribosomal subunit gene sequences. Such molecules can comprise at least 20, 25, 30, 35 or 40 consecutive nucleotides of these sequences, and can be obtained from any region of the disclosed sequences. The *Mycobacterium* 16S ribosomal subunit gene is approximately 1450 nucleotides in length. Nucleic acid molecules can be selected as probe sequences that comprise at least 20, 25, 30, 35 or 40 consecutive nucleotides of any of portions of the *Mycobacterium* 16S ribosomal subunit gene.

Purified: The term purified does not require absolute purity; rather, it is intended as a relative term. Thus, for example, a purified protein preparation is one in which the protein is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment comprising a complex mixture of oligonucleotides.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. A *Mycobacterium* 16S ribosomal subunit, isolated from one species, and the corresponding gene sequences, will possess a relatively high degree of sequence identity to a *Mycobacterium* 16S ribosomal subunit, isolated from another species, when aligned using standard methods.

Methods of alignment of sequences for comparison are well known in the art. Various programs and alignment algorithms are described in: Smith & Waterman (1981) *Adv. Appl. Math.* 2:482; Needleman & Wunsch (1970) *J. Mol. Biol.* 48:443; Pearson & Lipman (1988) *Proc. Natl. Acad. Sci. USA* 85:2444; Higgins & Sharp (1988) *Gene,* 73:23744; Higgins & Sharp (1989) *CABIOS* 5:151-3; Corpet et al. (1988) *Nuc. Acids Res.* 16:10881-90; Huang et al. (1992) *Computer Appls. Biosc.* 8:155-65; and Pearson et al. (1994) *Meth. Mol. Bio.* 24:307-31. Altschul et al. (1990) *J. Mol. Biol.* 215:403-10, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

For comparisons of nucleic acid sequences, sequence identity can be determined by comparing the nucleotide sequences of two nucleic acids using the BLAST sequence analysis software, for instance, the NCBI BLAST 2.0 program gapped blastn set to default parameters. (One example of such default settings would be: expect=10, filter=default, descriptions=500 pairwise, alignments=500, alignment view=standard, gap existence cost=11, per residue existence=1, per residue gap cost=0.85). These methods can be used to determine sequence identity over short windows, such as over the first 600 base pairs of the *Mycobacterium* 16S ribosomal subunit.

An indication that two nucleic acid molecules are closely related is that the two molecules hybridize to each other under stringent conditions.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater identity to the reference sequence will show increasing percentage identities when assessed by this method, such as at least 70%, 75%, 80%, 85%, 90%, 95%, 98%, 99% sequence identity, when using gapped blastp with databases such as the nr or swissprot database. Queries searched with the blastn program are filtered with DUST (Hancock and Armstrong, 1994, *Comput. Appl. Biosci.* 10:67-70). Other programs use SEG. When less than the entire sequence is being compared for sequence identity, homologs typically possess at least 75% sequence identity over short windows of 10-20 amino acids, and may possess sequence identities of at least 85%, 90%, 95% or 98% depending on their identity to the reference sequence. Methods for determining sequence identity over such short windows are described at the NCBI web site. One of skill in the art will appreciate that these sequence identity ranges are provided for guidance only; it is entirely possible that significant homologs can be obtained that fall outside of the ranges provided.

Variant oligonucleotides and variant analogs: A variation of an oligonucleotide or an oligonucleotide analog is an oligomer having one or more base substitutions, one or more base deletions, and/or one or more base insertions, so long as the oligomer substantially retains the activity of the original oligonucleotide or analog, or has sufficient complementarity to a target sequence.

A variant oligonucleotide or analog may also hybridize with the target DNA or RNA, under stringency conditions as described above. A variant oligonulceotide or analog also exhibits sufficient complementarity with the target DNA or RNA of the original oligonucleotide or analog as described above.

II. Detection of Mycobacteria in Clinical Specimens

The system described herein is based on the conserved nature of the *Mycobacterium* gene encoding the 16S ribosomal subunit. Briefly, the techniques include collecting a sample, amplifying nucleic acid in the sample using primers that amplify a specific *Mycobacterium* sequence from more than one species of *Mycobacterium* gene (e.g., 16S ribosomal subunit sequences), and identifying the *Mycobacterium* species present in the sample using species-specific probes for the specific *Mycobacterium* gene sequences (e.g. probes that identify the 16S ribosomal subunit sequences).

a. Clinical Specimens

Appropriate specimens for use with the current disclosure in detection of *Mycobacterium* include any conventional clinical samples, for instance blood or blood-fractions (e.g., serum), and bronchoalveolar lavage (BAL), sputum, and induced sputum samples. Techniques for acquisition of such samples are well known in the art. See, for instance, Schluger et al. (*J. Exp. Med.* 176:1327-33, 1992) (collection of serum samples); Bigby et al. (*Am. Rev. Respir. Dis.* 133:515-8, 1986) and Kovacs et al. (*NEJM* 318:589-93, 1988) (collection of sputum samples); and Ognibene et al. (*Am. Rev. Respir. Dis.* 129:929-32, 1984) (collection of bronchoalveolar lavage, BAL).

In addition to conventional methods, oral washing sequences (Helweg-Larsen et al., *J. Clin. Microbiol.* 36:2068-72, 1998) provide a non-invasive technique for acquiring appropriate samples to be used in nucleic acid amplification of *Mycobacterium*. Oral washing involves having the subject gargle with 50 cc of normal saline for 10-30 seconds and then expectorate the wash into a sample cup.

Serum or other blood fractions can be prepared in the conventional manner. About 200 µL of serum is an appropriate amount for the extraction of DNA for use in amplification reactions. See also, Schluger et al., *J. Exp. Med.* 176:1327-33, 1992; Ortona et al., *Mol. Cell Probes* 10: 187-90, 1996.

Once a sample has been obtained, the sample can be used directly, or concentrated (e.g. by centrifugation or filtration) and an amplification reaction performed. Alternatively, the nucleic acid can be extracted using any conventional method prior to amplification. For example, rapid DNA preparation can be performed using a commercially available kit (e.g., the InstaGene Matrix, BioRad, Hercules, Calif.; the NucliSens isolation kit, Organon Teknika, Netherlands). In one embodiment, the DNA preparation technique chosen yields a nucleotide preparation that is accessible to, and amenable to, nucleic acid amplification.

b. Amplification of *Mycobacterium* Nucleic Acid

*Mycobacterium* nucleic acid can be amplified from target *Mycobacterium* gene sequences from the clinical sample prior to detection. In one embodiment, DNA sequences are amplified. In another embodiment, RNA sequences are amplified.

Any nucleic acid amplification method can be used. In one specific, non-limiting example, polymerase chain reaction (PCR) is used to amplify the mycobacterial nucleic acid sequences. In another specific, non-limiting example, RT-PCR can be used to amplify the *Mycobacterium* nucleic acid sequences. In a third specific, non-limiting example, transcription-mediated amplification (TMA) can be used to amplify the mycobacterial nucleic acid sequences. In one embodiment UTP is used in any amplification protocols.

In another embodiment, the target *Mycobacterium* nucleic acid sequences are the sequences of the *Mycobacterium* 16S ribosomal subunit. In one embodiment, the target sequence for amplification is the region from about base pair 100 to about base pair 600 of a *Mycobacterium* 16S ribosomal gene (e.g., Genbank Accession No. AJ131120, herein incorporated by reference, SEQ ID NO: 34). In one specific non-limiting example, the region form about base pair 132 to about base pair 582 of the *Mycobacterium* 16S ribosomal subunit gene is the target sequence for amplification. In another specific, non-limiting example, the region from about base pair 123 to about base pair 573 is the target sequence for amplification (e.g. Genbank Accession No. AF115387, *M. gordonae*, herein incorporated by reference, SEQ ID NO: 35). It should be noted that the sequence from about nucleotide 507 to about nucleotide 603 is identical in *M. tuberculosis, M. bovis, M. Bovis* BCG, *M. avium, M. intracellulare, M. Kansasii, M. gastri, M. Parptuberculosis, M. malmoesne, M. szugai, M. gordonae, M. leprae, M. ulcerans, M. asiaticum*, and *M. scrofulaceum*. The identity of these sequences allows primers from this region to be used to amplify all of these species of Mycobacteria with the same primers.

A pair of primers are utilized in the amplification reaction. One or both of the primers can be end-labeled (e.g. radiolabeled, fluoresceinated, or biotinylated). The pair of primers includes an upstream primer (which binds 5' to the downstream primer) and a downstream primer (which binds 3' to the upstream primer). In one embodiment, either the upstream primer or the downstream primer is labeled. One specific, non-limiting example of a primer label is a biotinylated downstream primer.

In one embodiment, the pair of primers used in the amplification reaction are *Mycobacterium*-genus selective primers, which permits amplification of nucleic acid from virtually all members of the *Mycobacterium* genus. Specific non-limiting examples of *Mycobacterium* genus selective primers that bind to *Mycobacterium* 16S ribosomal subunit gene sequences include: 5'-ggg-ata-agc-ctg-gga-aac-tgg-gtc-3' (Myco.up, SEQ ID NO: 1) and 5'-BIOTIN-ccc-tct-cag-gcc-ggc-tac-ccg-3' (Myco.dwn-Bio, SEQ ID NO: 2).

In one embodiment, the pair of primers used in the amplification reaction are *Mycobacterium* specific primers which permit amplification of nucleic acid from the most clinically relevant mycobacterial pathogens. Specific non-limiting examples of *Mycobacterium*-specific primers that bind to *Mycobacterium* 16S ribosomal subunit gene sequences include: upstream primer: SEQ ID NO: 1 and downstream primers: 5'-BIOTIN-cta-ccg-tca-atc-cga-gag-aac-ccg-3' (MycoTB-Bio, SEQ ID NO: 3); 5'-BIOTIN-cta-ccg-tca-gcc-cga-gaa-aac-ccg-3' (MycoGOR-Bio, SEQ ID NO: 4); 5'-BIOTIN-cta-ccg-tca-cca-cga-gaa-aac-ccg-3' (MycoXEN-Bio, SEQ ID NO: 5); 5'-BIOTIN-cta-ccg-tca-atc-cga-gaa-aac-ccg-3' (MycoMAC-Bio, SEQ ID NO: 6); 5'-BIOTIN-ggt-ttc-acg-aac-aac-gcg-aca-aac-cac-c-3' (MycoGENA.1-Bio, SEQ ID NO: 7); 5'-BIOTIN-ttc-acg-aac-aac-gcg-aca-aac-cac-c-3' (MycoGENA.2-Bio, SEQ ID NO:

8) and 5'-BIOTIN-cta-ccg-tca-atc-cga-gaa-aac-cca-g-3' (MycoLEPR-Bio, SEQ ID NO: 9).

An additional pair of primers can be included in the amplification reaction as an internal control. These primers are designed to amplify nucleic acid from all samples, and serve to provide confirmation of appropriate amplification. One of skill in the art will readily be able to identify primer pairs to serve as internal control primers Alternatively, a target nucleic acid including primer hybridization sites can be constructed and included on the amplification reactor. These target sequences serves as a control for amplification when appropriate primers are added to the amplification reaction. A target probe is then included in the *Mycobacterium* detection array to detect the efficiency of the amplification reaction and the appropriateness of the hybridization conditions.

c. Arrays for Detection of *Mycobacterium* Nucleic Acid Sequences

Arrays can be used to detect the presence of amplified specific *Mycobacterium* sequences, such as 16S ribosomal subunit sequences, using specific oligonucleotide probes. The arrays herein termed "*Mycobacterium* detection arrays," are used to detect the presence of *Mycobacterium*. A predetermined set of oligonucleotide probes are attached to the surface of a solid support for use in detection of the amplified *Mycobacterium* nucleic acid sequences (for example, see FIG. 1). Additionally, if an internal control nucleic acid sequence was amplified in the amplification reaction (see above), an oligonucleotide probe can be included to detect the presence of this amplified nucleic acids.

The oligonucleotides specifically bind sequences amplified in the amplification reaction. Thus, sequences of use with the method, when 16S ribosomal subunit nucleic acid sequences are amplified, are oligonucleotide probes that recognize the 16S ribosomal subunit nucleic acid from only one species of *Mycobacterium*. Such sequences can be determined by examining the sequences of the different species, and choosing primers that specifically anneal to a particular species, but not others.

One of skill in the art will be able to identify other *Mycobacterium* oligonucleotide probes that can be attached to the surface of a solid support for the detection of other amplified *Mycobacterium* nucleic acid sequences (e.g. *Mycobacterium* DNA sequences).

The methods and apparatus in accordance with the present disclosure takes advantage of the fact that under appropriate conditions oligonucleotides form base-paired duplexes with oligonucleotides which have a complementary base sequence. The stability of the duplex is dependent on a number of factors, including the length of the oligonucleotides, the base composition, and the composition of the solution in which hybridization is effected. The effects of base composition on duplex stability may be reduced by carrying out the hybridization in particular solutions, for example in the presence of high concentrations of tertiary or quaternary amines.

The thermal stability of the duplex is also dependent on the degree of sequence similarity between the sequences. By carrying out the hybridization at temperatures close to the anticipated $T_m$'s of the type of duplexes expected to be formed between the target material(s) and the oligonucleotides bound to the array, the rate of formation of mismatched duplexes may be substantially reduced.

The length of each probe sequence employed in the array can be selected to optimize binding of target *Mycobacterium* nucleic acid sequences. An optimum length for use with a particular *Mycobacterium* nucleic acid sequence under specific screening conditions can be determined empirically. Thus, the length for each individual element of the set of *Mycobacterium* probe sequences comprising the array can be optimized for screening. In one embodiment, the *Mycobacterium* probes are from about 20 to about 35 nucleotides in length. In another embodiment, the *Mycobacterium* oligonucleotide probes are from about 25 to about 40 nucleotides in length The sequences forming the array can be directly linked to the support. Alternatively, the *Mycobacterium* oligonucleotide probes can be attached to the support by non-*Mycobacterium* sequences such as oligonucleotides or other molecules that serve as spacers or linkers to the solid support.

In one embodiment, the probe oligonucleotides in the array are probes for *Mycobacterium* 16S ribosomal subunit nucleic acids. Specific, non-limiting example of oligonucleotide probes for *Mycobacterium* 16S ribosomal subunit nucleic acids include, but are not limited to: 3'-tc-ctg-tac-aca-gga-cac-cag-gat-aag-cc-5' which can be used to detect *M. gordonae* (SEQ ID NO: 10), 3'-tt-tct-gta-cgc-gga-ttt-cca-gga-tag-5' which can be used to detect *M. intracellulare*-1 (SEQ ID NO: 11); 3'-tt-tct-gta-cgc-aga-ttt-cca-gga-tag-5' which can be used to detect *M. intracellulare*-2 (SEQ ID NO: 12); 3'-t-ctt-ctg-tac-gca-gaa-ctc-cag-gat-5' which can be used to detect *M. avium/M. paratuberculosis* (SEQ ID NO: 13); 3'-gat-ttc-gcg-aaa-ggt-ggt-gtt-ctg-5' which can be used to detect *M. tuberculosis* (SEQ ID NO: 14); 3'-ggt-gtc-ctg-tac-tta-ggg-cac-cag-5' which can be used to detect *M. ulcerans/M. marinum* (SEQ ID NO: 15); 3'-gtt-ccg-tac-gcg-gtt-cac-cag-gat-5' which can be used to detect *M. kansasii/M. gastri/M. scrofulaceum* (SEQ ID NO: 16) 3'-cgt-acg-cgg-aac-tcc-agg-ata-ggc-5' which can be used to detect *M. haemophilum* (SEQ ID NO: 17); 3'-gtg-ttc-tgt-acg-cgg-aac-ttc-agg-5' which can be used to detect *M. leprae* (SEQ ID NO: 18); 3'-gtt-ttg-tac-gca-agg-cac-cag-tat-agg-5' which can be used to detect *M. genavense* (SEQ ID NO: 19); and 3'-ggt-gta-cgc-gtc-tta-cca-gga-tag-gc-5' which can be used to detect *M. xenopi* (SEQ ID NO: 20).

Other suitable probes include, but are not limited to: 5'-gaa-tat-gac-cgc-gct-ctt-cat-ggg-gtg-tg-3' which can be used to detect *M. fortuitum*-1 (SEQ ID NO: 21); 5'-ca-cac-ccc-atg-aag-agc-gcg-gtc-ata-ttc-3' which can be used to detect *M. fortuitum*-1RC (SEQ ID NO: 22); 5'-gaa-tat-gac-cac-gcg-ctt-cat-ggt-gtg-tg-3' which can be used to detect *M. fortuitum*-2 (SEQ ID NO: 23); 5'-ca-cac-acc-atg-aag-cgc-gcg-gtc-ata-ttc-3' which can be used to detect *M. fortuitum*-2RC (SEQ ID NO: 24); 5'-gaa-tat-gac-cgc-gca-ctt-cct-ggt-gtg-tg-3' which can be used to detect *M. fortuitum*-3 (SEQ ID NO: 25); 5'-ca-cac-acc-agg-aag-tgc-gcg-gtc-ata-ttc-3' which can be used to detect *M. fortuitum*-3RC (SEQ ID NO: 26); 5'-gaa-tat-gac-cgc-gca-ctt-cct-ggt-gtg-tg-3' which can be used to detect *M. fortuitum*-4 (SEQ ID NO: 27); 5'-ca-cac-acc-agg-aag-tgc-gcg-gtc-ata-ttc-3' which can be used to detect *M. fortuitum*-4RC (SEQ ID NO: 28); 5'-gga-tag-gac-cac-gcg-ctt-cat-ggt-gtg-tg-3' which can be used to detect *M. fortuitum*-5 (SEQ ID NO: 29); 5'-ca-cac-acc-atg-aag-cgc-gtg-gtc-cta-tcc-3' which can be used to detect *M. fortuitum*-5RC (SEQ ID NO: 30); 5'-gaa-cgg-aaa-ggc-cct-tcg-ggg-tac-t-3' which can be used to detect *M. chelonae*-1 (SEQ ID NO: 31); 5'-gaa-cgg-aaa-ggc-ttc-ggg-gta-ctc-g-3' which can be used to detect *M. chelonae*-2 (SEQ ID NO: 32); and 5'-gaa-cgg-aaa-ggc-cct-tcg-ggg-tgc-t-3' which can be used to detect *M. chelonae*-3 (SEQ ID NO: 33).

The solid support can be formed from an organic polymer. Suitable materials for the solid support include, but are not limited to: polypropylene, polyethylene, polybutylene, polyisobutylene, plybutadiene, polyisoprene, polyvinylpyrrolidine, polytetrafluroethylene, polyvinylidene difluoride, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567, herein incorporated by reference).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert, such that at the termination of biomolecular synthesis, areas on the support not occupied by the biomolecules are not amenable to non-specific binding, or when non-specific binding occurs, such materials can be readily removed from the surface without removing the biomolecules.

In one embodiment, the solid support surface is polypropylene. Polypropylene is chemically inert and hydrophobic. Non-specific binding is generally avoidable, and detection sensitivity is improved. Polypropylene has good chemical resistance to a variety of organic acids (i.e., formic acid), organic agents (i.e. acetone or ethanol), bases (i.e. sodium hydroxide), salts (i.e. sodium chloride), oxidizing agents (i.e. peracetic acid), and mineral acids (i.e. hydrochloric acid). Polypropylene also provides a low fluorescence background, which minimizes background interference and increases the sensitivity of the signal of interest.

A surface activated organic polymer can be the solid support surface. In one specific non-limiting example, the surface activated organic polymer is a polypropylene material aminated via radio frequency plasma discharge. Such materials are easily utilized for the attachment of nucleotides, and thus are well suited for oligonucleotide synthesis. The amine groups on the activated organic polymers are reactive with nucleotides such that the nucleotides can be bound to the polymers. Alternatively, other reactive groups can be used (e.g., carboxylated, hydroxylated, thiolated, or active ester groups).

Figure 2A:
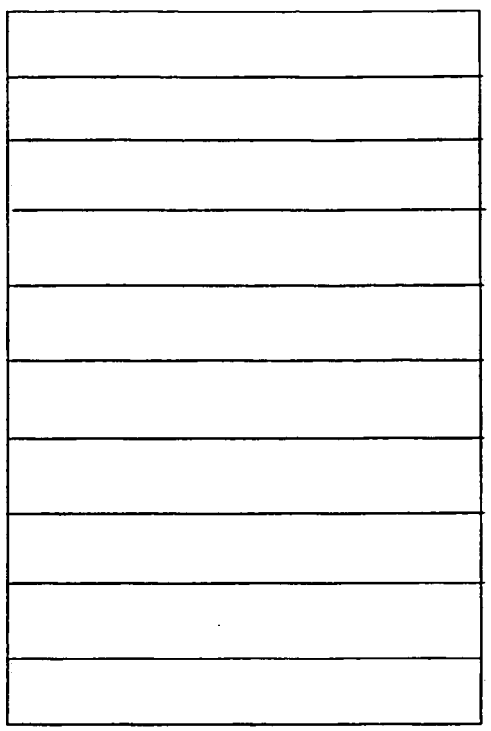
FIGS. 2A-2C are schematic drawings showing a top view of solid phase arrays, illustrating alternative embodiments of the pattern of *Mycobacterium* oligonucleotide probes attached to a solid support.
Figure 2B:
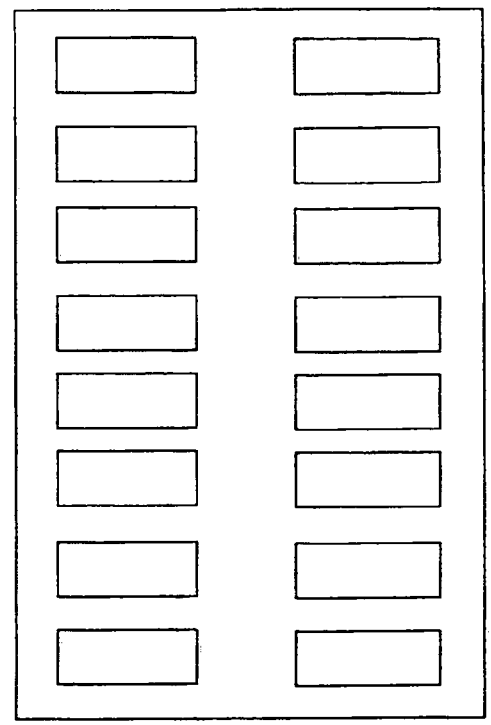
Figure 2C:
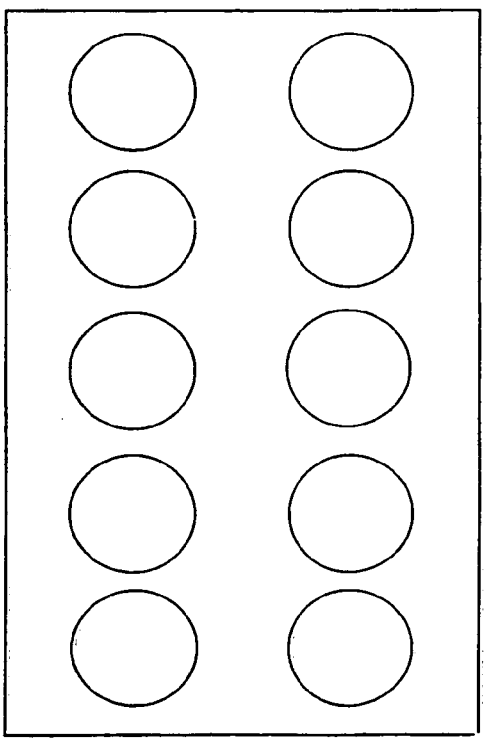

A wide variety of array formats can be employed in accordance with the present disclosure. One example includes a linear array of oligonucleotide bands, generally referred to in the art as a dipstick (see FIG. 2A and FIGS. 3A-3H). Another suitable format comprises a two-dimensional pattern of discrete cells (e.g., 4096 squares in a 64 by 64 array, see also FIGS. 2A-2C). As would be readily appreciated by those skilled in the art, other array formats including, but not limited to slot (rectangular) (FIG. 2B) and circular (FIG. 2C) arrays are equally suitable for use (see U.S. Pat. No. 5,981,185, herein incorporated by reference). In one embodiment, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. Particularly disclosed for preparation of arrays at this time are biaxially oriented polypropylene (BOPP) films; in addition to their durability, BOPP films exhibit a low background fluorescence.

The array formats of the present disclosure can be included in a variety of different types of formats. A "format" includes any format to which the solid support can be affixed, such as microtiter plates, test tubes, inorganic sheets, dipsticks, etc. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (e.g. the dipstick or slide) is stable to any materials into which the device is introduced (e.g. clinical samples, hybridization solutions, etc.).

The arrays of the present disclosure can be prepared by a variety of approaches which are known to those working in the field. Pursuant to one type of approach, the complete oligonucleotide probe sequences are synthesized separately and then attached to a solid support (see U.S. Pat. No. 6,013,789, herein incorporated by reference). In another embodiment, the sequences can be synthesized directly onto the support to provide the desired array (see U.S. Pat. No. 5,554,501, herein incorporated by reference). Suitable methods for covalently coupling oligonucleotides to a solid support and for directly synthesizing the oligonucleotides onto the support would be readily apparent to those working in the field; a summary of suitable methods can be found in Matson et al., *Anal. Biochem.* 217:306-10, 1994. In one embodiment, the oligonucleotides are synthesized onto the support using conventional chemical techniques for preparing oligonucleotides on solid supports (e.g., see PCT applications WO 85/01051 and WO 89/10977, or U.S. Pat. No. 5,554,501, herein incorporated by reference).

In one specific, non-limiting example, a polypropylene support (for example, a BOPP) is first surface aminated by exposure to an ammonia plasma generated by radiofrequency plasma discharge. The reaction of a phosphoramidite-activated nucleotide with the aminated membrane followed by oxidation with, e.g., iodine provides a base stable amidate bond to the support.

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one embodiment, the oligonucleotides are bound to the solid support by the 3' end. However, one of skill in the art will be able to determine whether the use of the 3' end or the 5' end of the oligonucleotide is suitable for bonding to the solid support. In general, the internal complementarity of an oligonucleotide probe in the region of the 3' end and the 5' end determines binding to the support. In general, the end of the probe with the most internal complementarity is bound to the support, thereby leaving the end with the least internal complementarity to bind to amplified *Mycobacterium* sequences.

d. Detection of *Mycobacterium* Nucleic Acid

In one embodiment, the oligonucleotide probes used in an amplification reaction are labeled (e.g. biotin labeled, radiolabeled, or enzymatically labeled). Alternatively, the amplified nucleic acid samples are end-labeled to form labeled amplified material. In one embodiment, the amplified mycobacterial nucleic acid is labeled by including labeled nucleotides in the amplification reactions. Methods for labeling nucleic acids are well known to one of skill in the art. For example, conventional methods for end-labeling nucleic acids are employed following the amplification reaction. Radioactive and fluorescent labeling methods, as well as other methods known in the art, are suitable for use with the present disclosure.

The labeled amplified *Mycobacterium* nucleic acid is applied to the *Mycobacterium* probe array under suitable hybridization conditions to form a hybridization complex. In one embodiment a pre-treatment solution of organic compounds, solutions that include organic compounds, or hot water, can be applied before hybridization (see U.S. Pat. No. 5,985,567, herein incorporated by reference).

Hybridization conditions for a given combination of array and target material can be optimized routinely in an empirical manner close to the $T_m$ of the expected duplexes, thereby maximizing the discriminating power of the method. Identification of the location in the array, such as a cell, in which binding occurs, permits a rapid and accurate identification of *Mycobacterium* sequences present in the amplified material (see below).

The hybridization conditions are selected to permit discrimination between matched and mismatched oligonucleotides. Hybridization conditions can be chosen to correspond to those known to be suitable in standard procedures for hybridization to filters and then optimized for use with the arrays of the disclosure. For example, conditions suitable for hybridization of one type of target would be adjusted for the use of other targets for the array. In particular, temperature is controlled to substantially eliminate formation of duplexes between sequences other than exactly complementary *Mycobacterium* sequences. A variety of known hybridization solvents can be employed, the choice being dependent on considerations known to one of skill in the art (see U.S. Pat. No. 5,981,185, herein incorporated by reference).

The developing and detecting of a hybridized complex in an array of oligonucleotide probes have been previously described (see U.S. Pat. No. 5,985,567, herein incorporated by reference). Briefly, developing and detection can include the steps of treating the hybridized complex with a conjugating solution, and treating the conjugated, hybridized complex with a detection reagent.

Once the amplified *Mycobacterium* nucleic acid has been hybridized with the oligonulceotide probes present in the *Mycobacterium* detection array the presence of the hybridization complex is detected. The developing and detection can include the use of a detection label.

The detection label is used to detect the signal of interest, and may be a radiolabel or a non-radiolabel. Non-radiolabels include, but are not limited to an enzyme, chemiluminescent compound, fluorescent compound, metal complex, hapten, enzyme, colorimetric agent, or a dye. The developing can include applying a buffer. In one embodiment, the buffer is sodium saline citrate, sodium saline phosphate, tetramethylammonium chloride, sodium saline citrate in ethylenediaminetetra-acetic, sodium saline citrate in sodium dodecyl sulfate, sodium saline phosphate in ethylenediaminetetra-acetic, sodium saline phosphate in sodium dodecyl sulfate, tetramethylammonium chloride in ethylenediaminetetra-acetic, tetramethylammonium chloride in sodium dodecyl sulfate, or combinations thereof. However, other suitable buffer solutions may also be used.

The developing and detecting step can further include the steps of treating the hybridized complex with a conjugating solution, and treating the conjugated, hybridized complex with a detection reagent. However, these steps do not need to be carried out when radiolabels are used with the target biomolecules.

The hybridized complex can be treated after hybridization with a conjugating solution to effect conjugation or coupling of the hybridized complex with the detection label. In one embodiment, the conjugating solution comprises streptavidin alkaline phosphatase, avidin alkaline phosphatase, or horseradish peroxidase. Specific, non-limiting examples of conjugating solutions include streptavidin alkaline phosphatase, avidin alkaline phosphatase, or horseradish peroxidase. The conjugated, hybridized complex can be treated with a detection reagent. In one embodiment, the detection reagent comprises enzyme-labeled fluorescence reagents or calorimetric reagents. In one specific non-limiting example, the detection reagent is enzyme-labeled fluorescence reagent (ELF) from Molecular Probes, Inc., Eugene, Oreg. The hybridized complex can then be placed on a detection device, such as an ultraviolet (UV) transilluminator (manufactured by UVP, Inc. of Upland, Calif.). The signal is developed and the increased signal intensity may be recorded with a recording device, such as a charge coupled device (CCD) camera (manufactured by Photometrics, Inc. of Tucson, Ariz.).

e. Kits

The present disclosure also provides for a kit for identifying the species of *Mycobacterium* present in a sample. In one embodiment, the kit includes a *Mycobacterium* detection array, a buffer solution, a conjugating solution for developing the signal of interest, and a detection reagent for detecting the signal of interest, each in separate packaging, such as a container. In another embodiment, the kit includes a plurality of *Mycobacterium* target nucleic acid sequences for hybridization with a *Mycobacterium* detection array to serve as positive control. The target nucleic acid sequences can include oligonucleotides such as deoxyribonucleic acid, ribonucleic acid, and peptide-nucleic acid, or may comprise polymerase chain reaction fragments. The kit can also optionally include an effective amount of a pre-treatment solution for application to the probe biomolecules to produce an amplified signal.

EXAMPLES

Without further elaboration, it is believed that one skilled in the art can, using the preceding description, utilize the present disclosure to its fullest extent. The following examples are illustrative only, and not limiting of the disclosure in any way whatsoever.

Example 1

Detection of *Mycobacterium* Nucleic Acid in a Sample

A successful detection and identification of a pathogenic species of mycobacteria in a subject's respiratory samples were achieved a using the device of the disclosure and the mycobacteria-specific primers disclosed herein. One upstream primer and four downstream primers were used for PCR amplification of nucleic acids in a patient sample as follows: upstream primer: SEQ ID NO: 1 and four downstream primers: MycoTB-Bio (SEQ ID NO: 3); MycoGOR-Bio (SEQ ID NO: 4): MycoXEN-Bio (SEQ ID NO: 5); and MycoMAC-Bio (SEQ ID NO: 6). The following conditions were used for the PCR amplification reaction: 10×PCR Buffer (final concentration 1×); 2.5 mM MgCl$_2$; 2.5 mg/ml BSA; 1 U UNG; 2.5 U Taq; 0.2 mM each dATP, dGTP, dCTP; 0.4 mM dUTP; 50 pmol each SEQ ID NO: 1, MycoTB-BIO (SEQ ID NO: 3), MycoGOR-BIO (SEQ ID NO: 4), MycoXEN-BIO(SEQ ID NO: 5), and MycoMAC-BIO (SEQ ID NO: 6). A 50 µl reaction was prepared. Other reaction volumes can also be prepared (e.g. 25, 20, or 5 µl reactions).

Alternatively, the following genus-selective primers were used: SEQ ID NOS: 1 and 2 under identical PCR conditions as described above, except that 50 pmol each SEQ ID NOS: 1 and 2 were used instead of the primers listed above.

With both sets of primers, the following amplification cycling protocol was used: 20° C. for 10 minutes; 94° C. for 2 minutes; then 35 cycles of 94° C. for 1 minute, 65° C. for 30 seconds, and 72° C. for 30 seconds. This was followed by 72° C. for 10 minutes and a hold at 4° C.

A PCR product was obtained using a concentrated sputum sample obtained from a subject, which was positive for acid-fast bacilli. The amplification products were hybridized to a *Mycobacterium* detection array including the probe sequences shown in SEQ ID NOS: 10-16.

The following hybridization procedure was used. The following components were added to a microfuge tube and inverted several times to mix: 950 µl 2×SSPE, 0.01% SDS; 50 µl PCR product (biotinylated); and 2 µl biotinylated dTTP-18 (0.01 µg/µl poly-T oligonucleotide, or 0.2 µg per reaction, which serves as a positive control). The *Mycobacterium* detection array in a strip form was trimmed and inserted into microfuge tube. The tube was placed in boiling water bath for two minutes then mmediately placed in a 50° C. heat block for one hour. The strip was transferred to a 50 ml Falcon tube containing 20-30 ml 2×SSC, 0.01% SDS and washed for five minutes with gentle agitation. A mixture of 990 µl 2×SSC and 10 µl TROPIX (prepared immediately prior to use) was pipetted into a microfuge tube and inverted several time to mix. The hybridized strip was placed into the tube and incubated for approximately one hour at room temperature (RT) with gentle agitation. The hybridized strip was washed three times, 5 minutes per wash, with 20-30 ml 2×SSC, 0.01% SDS in a 50 ml Falcon tube with gentle agitation. ELF Component B (760 µl) was pipetted into a microfuge tube and 40 µl ELF Component A was added, and inverted several times to mix. These components are part of a commercially available reagent kit, and were prepared immediately prior to use. The strip was inserted into the microfuge tube and incubated for 30 minutes at RT (without agitation). The strip was rinsed briefly in 2×SSC buffer and signal was detected on the UV transilluminator box.

In this assay system the mycobacterial detection array showed the presence of nucleic acid corresponding to *Mycobacterium avium*. Another aliquot of the concentrate tested negative for *Mycobacterium tuberculosis* with the commercially available GenProbe MTD test. The identification of the acid-fast bacillus in the sample as *M. avium* was subsequently confirmed by a standard mycobacteriology work up.

Example 2

Specificity

Figure 3:
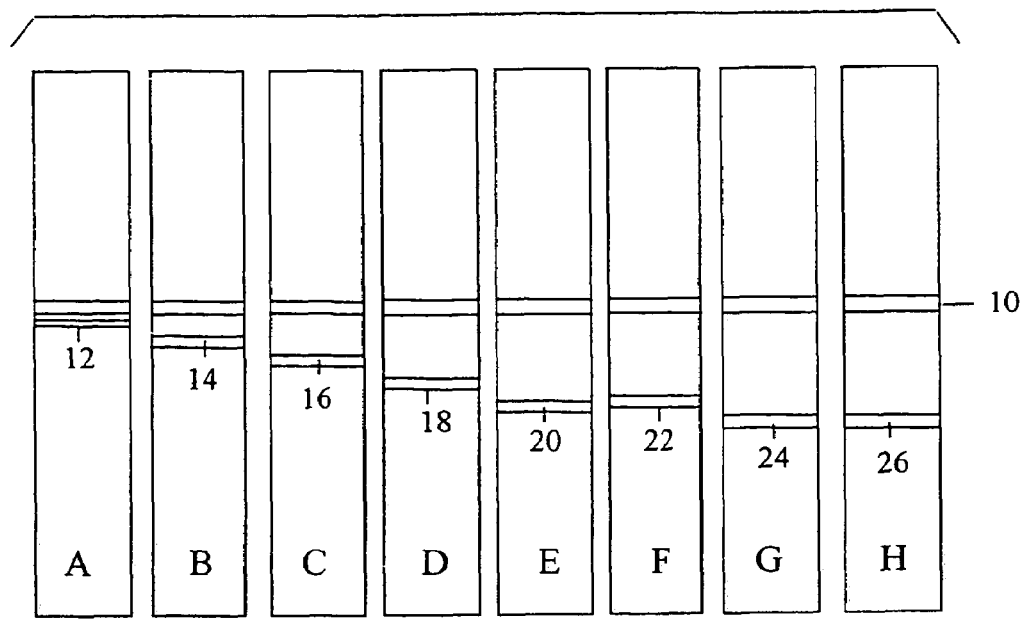
FIGS. 3A-H shows schematic drawings of the signals obtained using *Mycobacterium* detection arrays. A sample known to contain a mycobacterial species was amplified using mycobacterial specific primers, and hybridized to a solid phase array. A visible band (10) is shown as in each hybridization array as an 18 base pair poly-T biotin has successfully hybridized. This is a control band which demonstrates that amplification and hybridization have been performed successfully.
Figure 4:
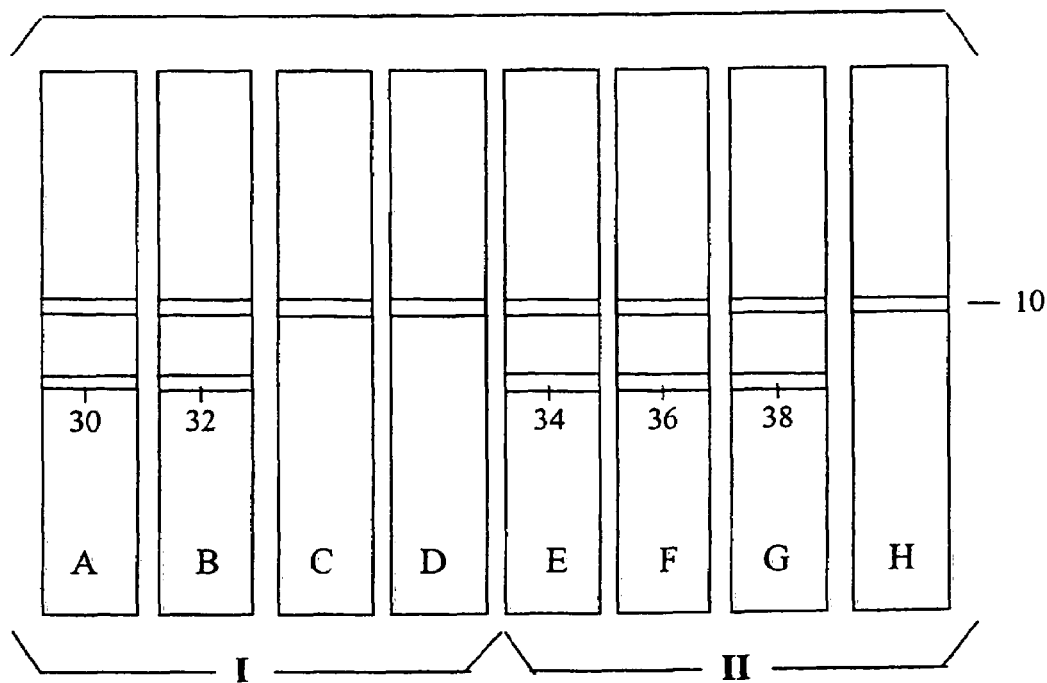
FIGS. 4A-4H are schematic drawings of *Mycobacterium* detection arrays which demonstrate the increased signal obtained using biotinylated dCTP.

Five additional mycobacterial species were tested using the protocol described in Example 1. The species tested, *M. gordonae, M. intracellulare, M. avium, M. tuberculosis, M. marinum*, and *M. kansasii*, collectively constitute about 90% of the patient isolates detected in many clinical mycobacteriology lab sections. To achieve specific hybridization of the PCR products from all these species, different variations of hybridization conditions were tested with the Mycobacterial detection array. In FIGS. 3A-H a visible band (10) is shown as in each hybridization array as an 18 base pair poly-T biotin has successfully hybridized. This is a control band which demonstrates that amplification and hybridization have been performed successfully. Specific hybridization reactions were demonstrated with nucleic acids amplified from known samples of *M. gordonae, M. intracellulare, M. avium, M. tuberculosis, M. marinum*, and *M. kansasii*. A single solid band lit up on each strip below the bright poly-A control band. The strips show each PCR product. FIGS. 1A-1H show a mycobacterium PCR product hybridizing only to its unique detection band as follows: *M. gordonae* (FIG. 3A, probe line 12), *M. intracellulare* from one isolate type (FIG. 3B, probe line 14), *M. avium* (FIG. 3C probe line 16), *M. tuberculosis* (FIG. 3D, probe line 18), *M. ulcerans* (FIG. 3E *M. ulcerans/M. marinum* probe line 20), *M. marinum* (FIG. 3F, *M. ulcearans/M. marinum* probe line 22), *M. kansasii* (FIG. 3G, *M. kansasii/M. gastri* probe line 24), and *M gastri* (FIG. 3H *M. kansasii/M. gastri* probe line 26).

Example 3

Signal Amplification Using dCTP-Biotin

The use of dCTP-biotin in the PCR amplifications was tested to determine if a greater signal is generated for a given amount of PCR product. Results with the *Mycobacterium* genus-selective primers PCR amplification products using the protocol shown in Example 1 showed approximately a 10-fold signal increase with a consequent similar reduction in the limit of detection with the strips. Similarly, the use of the dCTP-biotin assay modification with the mycobacteria-specific primer set shown in Example 1 also resulted in a 10-fold signal increase.

PCR was performed using the same amount of *M. tuberculosis* DNA as a template. Reaction I used the standard four nucleotides and one primer with biotin attached (FIGS. 4A-4D). Reaction II used biotin-labeled dCTP in the nucleotide mix (FIGS. 4E-4H). Two sets of four the *Mycobacterium* detection arrays were incubated with various dilutions of two amplification products from reactions using the same amount of *M. tuberculosis* DNA (see FIGS. 4A-4H). Ten-fold dilution series were made of each reaction (1:10 (FIGS. 4B and 4F), 1:100 (FIGS. 4C and 4G) and 1:1,000 (FIGS. 4D and 4H)) and hybridized to *Mycobacterium* detection arrays, which were then developed. At each dilution, the intensity of the band seen with the dCTP-biotin modification (bands 34, 36, and 38 in FIGS. 4E, 4F, and 4G, respectively) is clearly stronger than the corresponding band with the standard method (bands 30 and 32 in FIGS. 4A and 4B, respectively). In the dCTP-biotin series there is a faint band visible at the 1:1,000 dilution, while none is observed with the corresponding 1:1,000 dilution of the standard product. This suggests that the dCTP-biotin modification increases the sensitivity of the assay system by ten-fold.

Having illustrated and described the principles of the present disclosure by several specific examples, it should be apparent to one skilled in the art that the disclosure can be modified in arrangement and detail without departing from such principles. In view of the many possible embodiments to which the principles of our disclosure can be applied, it should be recognized that the illustrated embodiments are only examples of the disclosure and should not be taken as a limitation on the scope of the disclosure. Rather, the scope of the disclsoure is in accord with the following claims. We therefore claim as our invention all that comes within the scope and spirit of these claims.

We claim:

1. A method for species-specific identification of a *Mycobacterium*, comprising:

hybridizing a *Mycobacterium*-genus selective primer or a *Mycobacterium* specific primer to a sample;

amplifying *Mycobacterium*-specific nucleic acids from the sample utilizing the *Mycobacterium*-genus selective primer or the *Mycobacterium*-specific primer to produce amplified *Mycobacterium*-specific nucleic acids;

hybridizing the amplified *Mycobacterium*-specific nucleic acids to a solid phase nucleic acid array comprising a plurality of *Mycobacterium* species-specific probe oligonucleotides chemically linked to a polymeric solid support surface in a predetermined pattern, wherein at least one of the *Mycobacterium* species-specific probe oligonucleotides attached to the solid support surface has a sequence as consisting of SEQ ID NO: 14;

detecting a hybridization pattern of the amplified *Mycobacterium*-specific nucleic acid to the *Mycobacterium* species-specific probe oligonucleotides chemically linked to a solid support surface in a predetermined pattern; and identifying the species of *Mycobacterium* in the sample based on the hybridization pattern.

2. A method for identifying a species of *Mycobacterium* present in a sample, comprising:

hybridizing a plurality of single stranded *Mycobacterium* species-specific oligonucleotide probes chemically linked to a solid support surface in an array with a *Mycobacterium*-specific nucleic acid from the sample, to form a hybridization complex, wherein the *Mycobacterium*-specific nucleic acids are in solution and wherein at least one of the *Mycobacterium* species-specific oligonucleotides attached to the solid support surface has a sequence as consisting of SEQ ID NO: 14; and detecting the presence of the hybridization complex, wherein the presence of the hybridization complex in the array indicates the species of *Mycobacterium* present in the sample.

3. The method of claim 1, wherein the primer is a *Mycobacterium*-genus selective primer that has a sequence as consisting of SEQ ID NO: 1.

4. The method of claim 1, wherein the primer is a *Mycobacterium*-specific primer that has a sequence as consisting of SEQ ID NO: 1 or SEQ ID NO: 3.

5. The method of claim 1, wherein the *Mycobacterium* species comprises *M. gordonae, M intracellulare, M avium, M tuberculosis, M marinum,* or *M kansasii.*

6. The method of claim 1, wherein the amplified *Mycobacterium*-specific nucleic acids are labeled nucleic acids.

7. The method of claim 6, wherein the labeled nucleic acid is biotin-labeled nucleic acid.

8. The method of claim 7, wherein the detection comprises contacting the hybridized solid phase nucleic acid array with an avidin linked to a detectable reagent.

9. The method of claim 8, wherein the detectable reagent is a fluorescent reagent or a radio-labeled reagent.

10. The method of claim 2, further comprising amplifying the *Mycobacterium*-specific nucleic acid in the sample prior to the hybridization step.

11. The method of claim 10, wherein the amplification comprises hybridization with an oligonucleotide having a nucleic acid sequence as consisting of SEQ ID NO: 1 or SEQ ID NO: 3, or at least 15 contiguous nucleotides of either of these sequences.

12. The method of claim 2, wherein the solid support surface is a polymeric surface.

13. The method of claim 12, wherein the polymeric surface is a polypropylene surface.

14. The method of claim 2, wherein each *Mycobacterium* species-specific oligonucleotide probe has a 5' and a 3' end, and wherein at least one of the *Mycobacterium* species-specific oligonucleotide probes is chemically linked to the solid support surface by the 3' end.

* * * * *

SEQUENCE LISTING

<160> NUMBER OF SEQ ID NOS: 35

<210> SEQ ID NO 1
<211> LENGTH: 24
<212> TYPE: DNA
<213> ORGANISM: Artificial Sequence
<220> FEATURE:
<223> OTHER INFORMATION: Mycobacterium-specific oligonucleotide

<400> SEQUENCE: 1
gggataagcc tgggaaactg ggtc                          24

<210> SEQ ID NO 2
<211> LENGTH: 21
<212> TYPE: DNA
<213> ORGANISM: Artificial Sequence
<220> FEATURE:
<223> OTHER INFORMATION: Mycobacterium-specific oligonucleotide

<400> SEQUENCE: 2
ccctctcagg ccggctaccc g                             21

<210> SEQ ID NO 3
<211> LENGTH: 24
<212> TYPE: DNA
<213> ORGANISM: Artificial Sequence
<220> FEATURE:
<223> OTHER INFORMATION: Mycobacterium-specific oligonucleotide

<400> SEQUENCE: 3
ctaccgtcaa tccgagagaa cccg                          24

<210> SEQ ID NO 4
<211> LENGTH: 24
<212> TYPE: DNA
<213> ORGANISM: Artificial Sequence
<220> FEATURE:
<223> OTHER INFORMATION: Mycobacterium-specific oligonucleotide

<400> SEQUENCE: 4
ctaccgtcag cccgagaaaa cccg                          24

<210> SEQ ID NO 5
<211> LENGTH: 24
<212> TYPE: DNA
<213> ORGANISM: Artificial Sequence
<220> FEATURE:
<223> OTHER INFORMATION: Mycobacterium-specific oligonucleotide

<400> SEQUENCE: 5
ctaccgtcac cacgagaaaa cccg                          24

<210> SEQ ID NO 6
<211> LENGTH: 24
<212> TYPE: DNA
<213> ORGANISM: Artificial Sequence
<220> FEATURE:
<223> OTHER INFORMATION: Mycobacterium-specific oligonucleotide

<400> SEQUENCE: 6
ctaccgtcaa tccgagaaaa cccg                          24

<210> SEQ ID NO 7
<211> LENGTH: 28

```
<212> TYPE: DNA
<213> ORGANISM: Artificial Sequence
<220> FEATURE:
<223> OTHER INFORMATION: Mycobacterium-specific oligonucleotide

<400> SEQUENCE: 7
ggtttcacga acaacgcgac aaaccacc                                              28

<210> SEQ ID NO 8
<211> LENGTH: 25
<212> TYPE: DNA
<213> ORGANISM: Artificial Sequence
<220> FEATURE:
<223> OTHER INFORMATION: Mycobacterium-specific oligonucleotide

<400> SEQUENCE: 8
ttcacgaaca acgcgacaaa ccacc                                                 25

<210> SEQ ID NO 9
<211> LENGTH: 25
<212> TYPE: DNA
<213> ORGANISM: Artificial Sequence
<220> FEATURE:
<223> OTHER INFORMATION: Mycobacterium-specific oligonucleotide

<400> SEQUENCE: 9
ctaccgtcaa tccgagaaaa cccag                                                 25

<210> SEQ ID NO 10
<211> LENGTH: 28
<212> TYPE: DNA
<213> ORGANISM: Artificial Sequence
<220> FEATURE:
<223> OTHER INFORMATION: Mycobacterium-specific oligonucleotide

<400> SEQUENCE: 10
tcctgtacac aggacaccag gataagcc                                              28

<210> SEQ ID NO 11
<211> LENGTH: 26
<212> TYPE: DNA
<213> ORGANISM: Artificial Sequence
<220> FEATURE:
<223> OTHER INFORMATION: Mycobacterium-specific oligonucleotide

<400> SEQUENCE: 11
tttctgtacg cggatttcca ggatag                                                26

<210> SEQ ID NO 12
<211> LENGTH: 26
<212> TYPE: DNA
<213> ORGANISM: Artificial Sequence
<220> FEATURE:
<223> OTHER INFORMATION: Mycobacterium-specific oligonucleotide

<400> SEQUENCE: 12
tttctgtacg cagatttcca ggatag                                                26

<210> SEQ ID NO 13
<211> LENGTH: 25
<212> TYPE: DNA
<213> ORGANISM: Artificial Sequence
<220> FEATURE:
<223> OTHER INFORMATION: Mycobacterium-specific oligonucleotide

<400> SEQUENCE: 13
```
tcttctgtac gcagaactcc aggat                                           25

<210> SEQ ID NO 14
<211> LENGTH: 24
<212> TYPE: DNA
<213> ORGANISM: Artificial Sequence
<220> FEATURE:
<223> OTHER INFORMATION: Mycobacterium-specific oligonucleotide

<400> SEQUENCE: 14
gatttcgcga aggtggtgt tctg                                             24

<210> SEQ ID NO 15
<211> LENGTH: 24
<212> TYPE: DNA
<213> ORGANISM: Artificial Sequence
<220> FEATURE:
<223> OTHER INFORMATION: Mycobacterium-specific oligonucleotide

<400> SEQUENCE: 15
ggtgtcctgt acttagggca ccag                                            24

<210> SEQ ID NO 16
<211> LENGTH: 24
<212> TYPE: DNA
<213> ORGANISM: Artificial Sequence
<220> FEATURE:
<223> OTHER INFORMATION: Mycobacterium-specific oligonucleotide

<400> SEQUENCE: 16
gttccgtacg cggttcacca ggat                                            24

<210> SEQ ID NO 17
<211> LENGTH: 24
<212> TYPE: DNA
<213> ORGANISM: Artificial Sequence
<220> FEATURE:
<223> OTHER INFORMATION: Mycobacterium-specific oligonucleotide

<400> SEQUENCE: 17
cgtacgcgga actccaggat aggc                                            24

<210> SEQ ID NO 18
<211> LENGTH: 24
<212> TYPE: DNA
<213> ORGANISM: Artificial Sequence
<220> FEATURE:
<223> OTHER INFORMATION: Mycobacterium-specific oligonucleotide

<400> SEQUENCE: 18
gtgttctgta cgcggaactt cagg                                            24

<210> SEQ ID NO 19
<211> LENGTH: 27
<212> TYPE: DNA
<213> ORGANISM: Artificial Sequence
<220> FEATURE:
<223> OTHER INFORMATION: Mycobacterium-specific oligonucleotide

<400> SEQUENCE: 19
gttttgtacg caaggcacca gtatagg                                         27

<210> SEQ ID NO 20
<211> LENGTH: 26
<212> TYPE: DNA
<213> ORGANISM: Artificial Sequence

```
<220> FEATURE:
<223> OTHER INFORMATION: Mycobacterium-specific oligonucleotide

<400> SEQUENCE: 20
ggtgtacgcg tcttaccagg ataggc                                          26

<210> SEQ ID NO 21
<211> LENGTH: 29
<212> TYPE: DNA
<213> ORGANISM: Artificial Sequence
<220> FEATURE:
<223> OTHER INFORMATION: Mycobacterium-specific oligonucleotide

<400> SEQUENCE: 21
gaatatgacc gcgctcttca tggggtgtg                                       29

<210> SEQ ID NO 22
<211> LENGTH: 29
<212> TYPE: DNA
<213> ORGANISM: Artificial Sequence
<220> FEATURE:
<223> OTHER INFORMATION: Mycobacterium-specific oligonucleotide

<400> SEQUENCE: 22
cacaccccat gaagagcgcg gtcatattc                                       29

<210> SEQ ID NO 23
<211> LENGTH: 29
<212> TYPE: DNA
<213> ORGANISM: Artificial Sequence
<220> FEATURE:
<223> OTHER INFORMATION: Mycobacterium-specific oligonucleotide

<400> SEQUENCE: 23
gaatatgacc acgcgcttca tggtgtgtg                                       29

<210> SEQ ID NO 24
<211> LENGTH: 29
<212> TYPE: DNA
<213> ORGANISM: Artificial Sequence
<220> FEATURE:
<223> OTHER INFORMATION: Mycobacterium-specific oligonucleotide

<400> SEQUENCE: 24
cacacaccat gaagcgcgcg gtcatattc                                       29

<210> SEQ ID NO 25
<211> LENGTH: 29
<212> TYPE: DNA
<213> ORGANISM: Artificial Sequence
<220> FEATURE:
<223> OTHER INFORMATION: Mycobacterium-specific oligonucleotide

<400> SEQUENCE: 25
gaatatgacc gcgcacttcc tggtgtgtg                                       29

<210> SEQ ID NO 26
<211> LENGTH: 29
<212> TYPE: DNA
<213> ORGANISM: Artificial Sequence
<220> FEATURE:
<223> OTHER INFORMATION: Mycobacterium-specific oligonucleotide

<400> SEQUENCE: 26
cacacaccag gaagtgcgcg gtcatattc                                       29
```

<210> SEQ ID NO 27
<211> LENGTH: 29
<212> TYPE: DNA
<213> ORGANISM: Artificial Sequence
<220> FEATURE:
<223> OTHER INFORMATION: Mycobacterium-specific oligonucleotide

<400> SEQUENCE: 27
gaatatgacc gcgcacttcc tggtgtgtg                                29

<210> SEQ ID NO 28
<211> LENGTH: 29
<212> TYPE: DNA
<213> ORGANISM: Artificial Sequence
<220> FEATURE:
<223> OTHER INFORMATION: Mycobacterium-specific oligonucleotide

<400> SEQUENCE: 28
cacacaccag gaagtgcgcg gtcatattc                                29

<210> SEQ ID NO 29
<211> LENGTH: 29
<212> TYPE: DNA
<213> ORGANISM: Artificial Sequence
<220> FEATURE:
<223> OTHER INFORMATION: Mycobacterium-specific oligonucleotide

<400> SEQUENCE: 29
ggataggacc acgcgcttca tggtgtgtg                                29

<210> SEQ ID NO 30
<211> LENGTH: 29
<212> TYPE: DNA
<213> ORGANISM: Artificial Sequence
<220> FEATURE:
<223> OTHER INFORMATION: Mycobacterium-specific oligonucleotide

<400> SEQUENCE: 30
cacacaccat gaagcgcgtg gtcctatcc                                29

<210> SEQ ID NO 31
<211> LENGTH: 25
<212> TYPE: DNA
<213> ORGANISM: Artificial Sequence
<220> FEATURE:
<223> OTHER INFORMATION: Mycobacterium-specific oligonucleotide

<400> SEQUENCE: 31
gaacggaaag gcccttcggg gtact                                    25

<210> SEQ ID NO 32
<211> LENGTH: 25
<212> TYPE: DNA
<213> ORGANISM: Artificial Sequence
<220> FEATURE:
<223> OTHER INFORMATION: Mycobacterium-specific oligonucleotide

<400> SEQUENCE: 32
gaacggaaag gcttcggggt actcg                                    25

<210> SEQ ID NO 33
<211> LENGTH: 25
<212> TYPE: DNA
<213> ORGANISM: Artificial Sequence
<220> FEATURE:
<223> OTHER INFORMATION: Mycobacterium-specific oligonucleotide

<400> SEQUENCE: 33
gaacggaaag gcccttcggg gtgct                                          25

<210> SEQ ID NO 34
<211> LENGTH: 1524
<212> TYPE: DNA
<213> ORGANISM: Mycobacterium tuberculosis

<400> SEQUENCE: 34
agagtttgat cctggctcag gacgaacgct ggcggcgtgc ttaacacatg caagtcgaac    60
ggaaaggtct cttcggagat actcgagtgg cgaacgggtg agtaacacgt gggtgatctg   120
ccctgcactt cgggataagc ctgggaaact gggtctaata ccggatagga ccacgggatg   180
catgtcttgt ggtggaaagc gctttagcgg tgtgggatga gcccgcggcc tatcagcttg   240
ttggtgggt gacggcctac caaggcgacg acgggtagcc ggcctgagag ggtgtccggc    300
cacactggga ctgagatacg gcccagactc ctacgggagg cagcagtggg gaatattgca   360
caatgggcgc aagcctgatg cagcgacgcc gcgtggggga tgacggcctt cgggttgtaa   420
acctctttca ccatcgacga aggtccgggt tctctcggat tgacggtagg tggagaagaa   480
gcaccggcca actacgtgcc agcagccgcg gtaatacgta gggtgcgagc gttgtccgga   540
attactgggc gtaaagagct cgtaggtggt ttgtcgcgtt gttcgtgaaa tctcacggct   600
taactgtgag cgtgcgggcg atacgggcag actagagtac tgcaggggag actggaattc   660
ctggtgtagc ggtggaatgc gcagatatca ggaggaacac cggtggcgaa ggcgggtctc   720
tgggcagtaa ctgacgctga ggagcgaaag cgtgggagc gaacaggatt agataccctg    780
gtagtccacg ccgtaaacgg tgggtactag gtgtgggttt ccttccttgg gatccgtgcc   840
gtagctaacg cattaagtac cccgcctggg gagtacggcc gcaaggctaa aactcaaagg   900
aattgacggg ggcccgcaca agcggcggag catgtggatt aattcgatgc aacgcgaaga   960
accttacctg ggtttgacat gcacaggacg cgtctagaga taggcgttcc cttgtggcct  1020
gtgtgcaggt ggtgcatggc tgtcgtcagc tcgtgtcgtg agatgttggg ttaagtcccg  1080
caacgagcgc aaccccttgtc tcatgttgcc agcacgtaat ggtggggact cgtgagagac  1140
tgccggggtc aactcggagg aaggtgggga tgacgtcaag tcatcatgcc cttatgtcc   1200
agggcttcac acatgctaca atggccggta caaagggctg cgatgccgcg aggttaagcg  1260
aatccttaaa agccggtctc agttcggatc ggggtctgca actcgacccc gtgaagtcgg  1320
agtcgctagt aatcgcagat cagcaacgct gcggtgaata cgttcccggg ccttgtacac  1380
accgcccgtc acgtcatgaa agtcggtaac acccgaagcc agtggcctaa ccctcgggag  1440
ggagctgtcg aaggtgggat cggcgattgg gacgaagtcg taacaaggta gccgtaccgg  1500
aaggtgcggc tggatcacct cctt                                          1524

<210> SEQ ID NO 35
<211> LENGTH: 146
<212> TYPE: DNA
<213> ORGANISM: Mycobacterium gordonae

<400> SEQUENCE: 35
gccatcaccc caccaacaag ctgataggcc gcgggcccat cccacaccgc aaaagctttc    60
caccacagga catgtgttct gtggtcctat tcggtattag acccagtttc ccaggcttat   120
cccgatgtgc agggcagatt acccac                                        146